United States Patent
Al-Azmi

(10) Patent No.: US 9,668,908 B1
(45) Date of Patent: Jun. 6, 2017

(54) SPINE IMMOBILIZING STRETCHER

(71) Applicant: Mohammed Saad Farhan Al-Azmi, Salwa (KW)

(72) Inventor: Mohammed Saad Farhan Al-Azmi, Salwa (KW)

( * ) Notice: Subject to any disclaimer, the term of this patent is extended or adjusted under 35 U.S.C. 154(b) by 0 days.

(21) Appl. No.: 15/214,413

(22) Filed: Jul. 19, 2016

(51) Int. Cl.
| | |
|---|---|
| *A61G 1/01* | (2006.01) |
| *A61G 1/044* | (2006.01) |
| *A61F 5/37* | (2006.01) |
| *A61G 1/048* | (2006.01) |
| *A61G 1/04* | (2006.01) |

(52) U.S. Cl.
CPC ............. *A61F 5/3776* (2013.01); *A61G 1/01* (2013.01); *A61G 1/04* (2013.01); *A61G 1/044* (2013.01); *A61G 1/048* (2013.01)

(58) Field of Classification Search
CPC . A61G 1/00; A61G 1/01; A61G 1/013; A61G 1/04; A61G 1/044; A61G 1/048; A61G 7/065; A61G 7/075; A61G 7/0755; A61G 13/12; A61G 13/1245; A61G 13/125; A61F 5/37; A61F 5/3769; A61F 5/3776
USPC ...... 5/628, 627, 625, 648; 128/869, 870, 876
See application file for complete search history.

(56) References Cited

U.S. PATENT DOCUMENTS

| | | | |
|---|---|---|---|
| 722,456 A | 3/1903 | Reeves | |
| 2,272,681 A | 2/1942 | Smith, Jr. et al. | |
| 2,489,828 A * | 11/1949 | Springer | A61G 1/01 5/625 |
| 2,728,089 A * | 12/1955 | Hynes | A47C 19/027 5/659 |
| 3,158,875 A | 12/1964 | Fletcher | |
| 4,679,260 A * | 7/1987 | Frettem | A61G 1/01 5/627 |
| 4,910,818 A * | 3/1990 | Grabill | A47C 20/021 297/423.17 |
| 5,058,575 A | 10/1991 | Anderson | |
| 5,121,514 A | 6/1992 | Rosane | |
| 5,359,739 A * | 11/1994 | Rains | A47C 21/08 5/424 |
| 5,530,974 A * | 7/1996 | Rains | A47C 21/08 5/630 |
| 5,577,281 A | 11/1996 | Mital et al. | |
| 5,701,619 A | 12/1997 | Ullman | |
| 5,720,303 A * | 2/1998 | Richardson | A61G 1/01 128/870 |
| D506,710 S | 6/2005 | Hurtado | |

(Continued)

FOREIGN PATENT DOCUMENTS

FR         2 549 366 A1      1/1985

*Primary Examiner* — Robert G Santos
(74) *Attorney, Agent, or Firm* — Richard C. Litman

(57) ABSTRACT

The spine immobilizing stretcher is a stretcher for transporting a patient suffering from spinal trauma. The spine immobilizing stretcher includes a flexible sheet having opposed upper and lower surfaces and which is elongated in a longitudinal direction. The flexible sheet further has first and second laterally opposed side edges. A longitudinally extending sleeve is formed on the upper surface of the flexible sheet, and a plurality of straps are secured to the first side edge of the flexible sheet. The plurality of straps are releasably securable to the second side edge of the flexible sheet. A stabilizing board, which is preferably longitudinally adjustable, is removably received within the longitudinally extending sleeve.

6 Claims, 3 Drawing Sheets

(56) References Cited

U.S. PATENT DOCUMENTS

| | | | | |
|---|---|---|---|---|
| 8,905,035 B2* | 12/2014 | Wilson | ............... | A61F 5/3769 |
| | | | | 128/845 |
| 2012/0186588 A1* | 7/2012 | Wilson | ............... | A61F 5/3769 |
| | | | | 128/845 |

\* cited by examiner

SPINE IMMOBILIZING STRETCHER

BACKGROUND OF THE INVENTION

1. Field of the Invention

The present invention relates generally to medical equipment, and particularly to a stretcher for immobilizing and supporting the spine of a patient suffering from spinal trauma.

2. Description of the Related Art

When a patient suffers from a spinal injury, or when a spinal injury is suspected, great care must be taken to immobilize the patient during transport so as not to worsen the spinal injury. The most common tool for transporting a patient with a spinal injury is the spinal board (sometimes referred to as a "back board"), which is a rigid plank with straps for holding the patient in place. In use, emergency personnel place the spinal board adjacent the patient and then gently lift the patient onto the board, where the patient is then secured and immobilized. Unfortunately, even the lifting of the patient onto the board can provide sufficient movement to exacerbate the patient's injuries. Thus, a spine immobilizing stretcher addressing the aforementioned problems is desired.

SUMMARY OF THE INVENTION

The spine immobilizing stretcher is a stretcher for transporting a patient suffering from spinal trauma. The spine immobilizing stretcher includes a flexible sheet having opposed upper and lower surfaces and which is elongated in a longitudinal direction. The flexible sheet further has first and second laterally opposed side edges. A longitudinally extending sleeve is formed on the upper surface of the flexible sheet, and a plurality of straps are secured to the first side edge of the flexible sheet. The plurality of straps are releasably securable to the second side edge of the flexible sheet. A stabilizing board, which is preferably longitudinally adjustable, is removably received within the longitudinally extending sleeve.

In use, the flexible sheet is slid under a patient suffering from spinal trauma such that the patient rests on the upper surface thereof. The flexible sheet is slid under the patient such that the patient's spine is positioned on and along the longitudinally extending sleeve. The stabilizing board is then inserted into the longitudinally extending sleeve to support and immobilize the patient's spine without moving the patient. The flexible sheet may then be wrapped around the patient and secured via the straps, providing secure and stable transport for the patient.

These and other features of the present invention will become readily apparent upon further review of the following specification and drawings.

BRIEF DESCRIPTION OF THE DRAWINGS

Unless otherwise indicated, similar reference characters denote corresponding features consistently throughout the attached drawings.

DETAILED DESCRIPTION OF THE PREFERRED EMBODIMENTS

Figure 1:
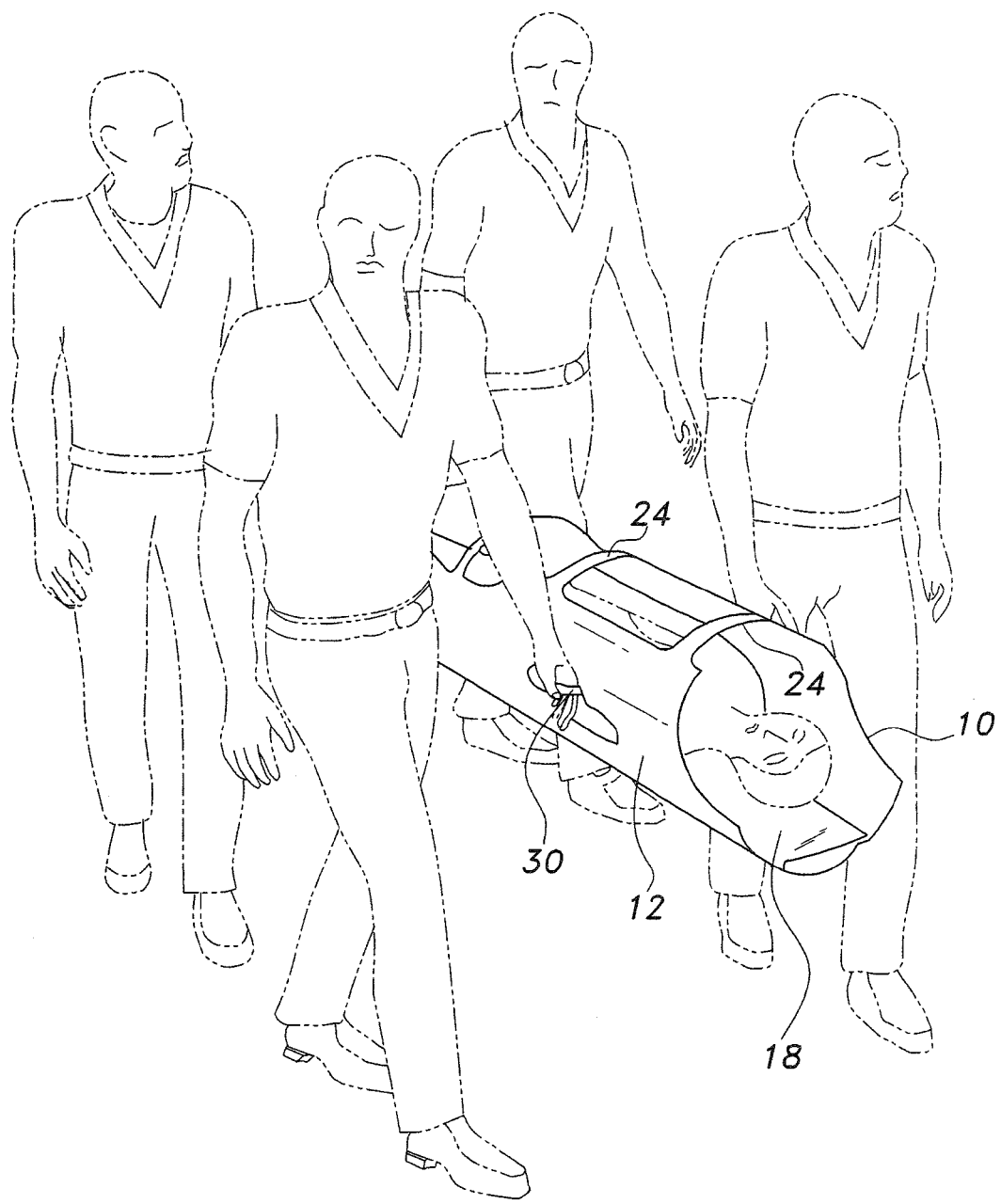
FIG. 1 is an environmental perspective view of a spine immobilizing stretcher according to the present invention.
Figure 2:
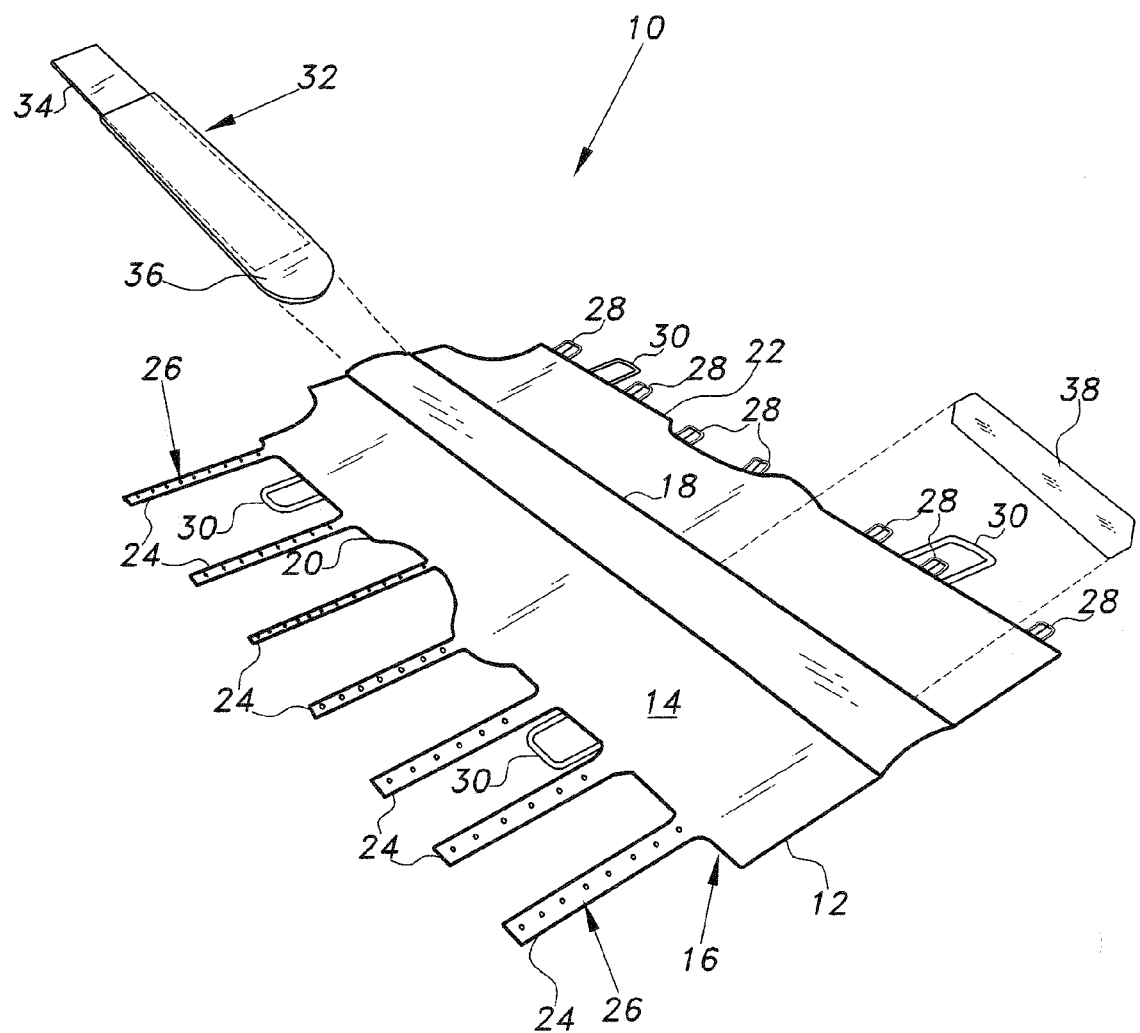
FIG. 2 is an exploded perspective view of the spine immobilizing stretcher according to the present invention.

The spine immobilizing stretcher 10 is a stretcher for transporting a patient suffering from spinal trauma. As shown in FIG. 1, the spine immobilizing stretcher 10 wraps around the body of a patient suffering or suspected of suffering from spinal trauma, thus immobilizing the patient during transport and, as will be described in greater detail below, providing stabilization and support specifically for the patient's spine. As best shown in FIG. 2, the spine immobilizing stretcher 10 includes a flexible sheet 12 having opposed upper and lower surfaces 14, 16, respectively, and which is elongated in a longitudinal direction. The flexible sheet 12 is elongated in the direction corresponding to the length of the patient's body. The flexible sheet 12 further includes first and second laterally opposed side edges 20, 22, respectively. It should be understood that the overall contouring and relative dimensions of flexible sheet 12 are shown in FIG. 2 for exemplary purposes only. Further, it should be understood that flexible sheet 12 may be formed from any suitable flexible and supportive material, such as plastic, canvas or the like.

A longitudinally extending sleeve 18 is formed on the upper surface 14 of the flexible sheet 12 and may be secured in any suitable manner, such as by stitching or the like. Additionally, a plurality of straps 24 are secured to the first side edge 20 of the flexible sheet 12, as shown. The plurality of straps 24 are releasably securable to the second side edge 22 of flexible sheet 12, such that the flexible sheet 12 may be wrapped securely around the patient, as in the configuration, as illustrated in FIG. 1. It should be understood that straps 24 may be releasably secured to the second side edge 22 by any suitable releasable fastener. For example, buckles 28 may be secured to the second side edge 22 and configured to engage openings 26 formed in the straps 24. It should be understood that any type of releasable fastener may be used, such as hook and loop fasteners or the like, and that buckles 28 are shown for exemplary purposes only.

A stabilizing board 32 is removably received within the longitudinally extending sleeve 18 for supporting, stabilizing and immobilizing the patient's spine. The stabilizing board 32 may be formed from any suitable type of rigid material for providing sufficient support to the patient's spine. Preferably, the stabilizing board 32 is adjustable along the longitudinal direction, relative to the length of the elongated sheet 12, allowing the stabilizing board 32 to have an adjustable length. The stabilizing board 32 is adjustable, both for purposes of storage and transport when not in use, and for allowing the stabilizing board 32 to be used with a variety of patients having different sizes and body types. The stabilizing board 32 may include a plurality of stabilizing members telescopically engaging one another. In FIG. 2, first and second stabilizing members 34, 36 are shown in a telescopic arrangement (with first member 34 being slidable within second member 36), though it should be understood that any suitable number of stabilizing members may be utilized and that, alternatively, stabilizing board 32 may have any suitable type of adjustable configuration.

Further, handles 30 are preferably secured to the first and second side edges 20, 22, allowing the stretcher 10 to be carried, as in the example of FIG. 1. Although a pair of handles 30 are shown secured to each of first and second side edges 20, 22, it should be understood that any suitable number of handles 30 may be used. Additionally, a cushion 38 is preferably provided for removable positioning between the legs of the patient, thus further preventing unintentional movement or repositioning of the patient's legs during transport.

Figure 3:
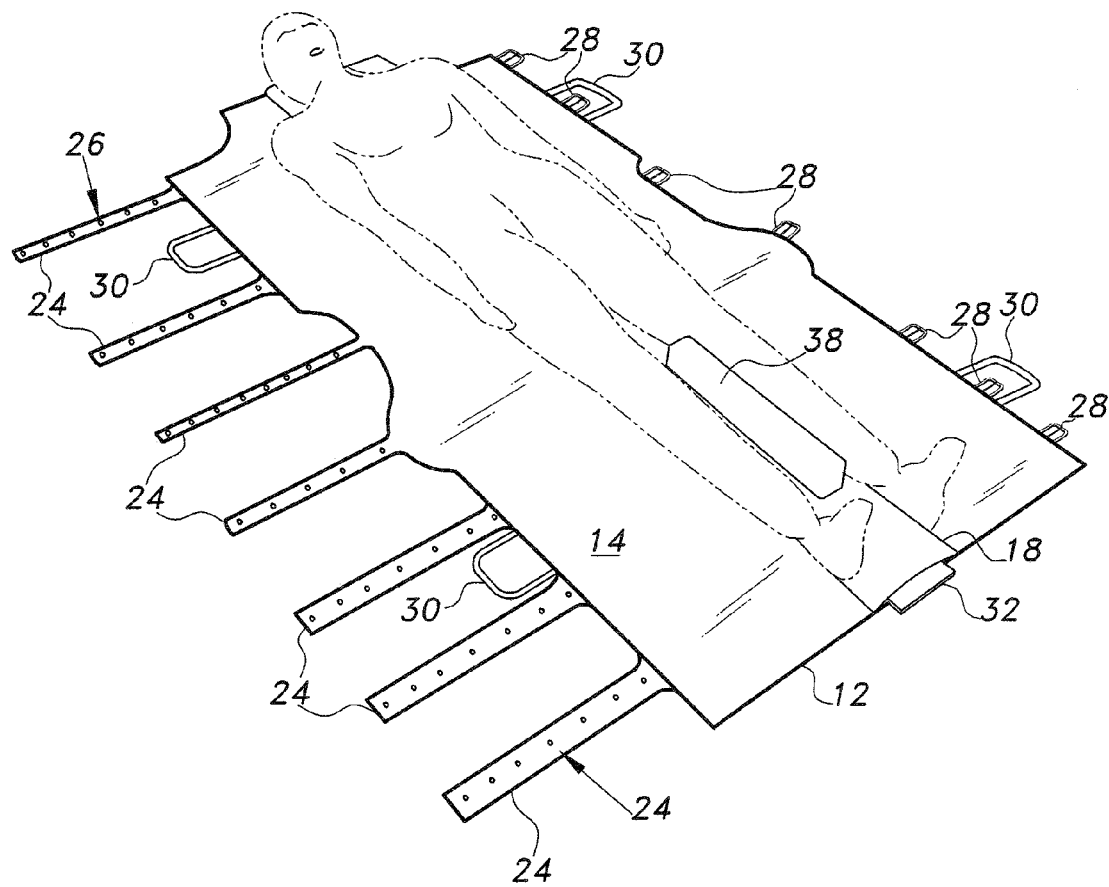
FIG. 3 is a perspective view of the spine immobilizing stretcher supporting a patient to be transported.

In use, as illustrated in FIG. 3, the flexible sheet 12 is slid under a patient suffering from spinal trauma such that the patient rests on the upper surface 14. The flexible sheet 12 is slid under the patient such that the patient's spine is positioned on and along the longitudinally extending sleeve 18. The stabilizing board 32 is then inserted into the longitudinally extending sleeve 18 to support and immobilize the patient's spine without moving the patient. The flexible sheet 12 may then be wrapped around the patient and secured via the straps 24, providing secure and stable transport for the patient. As shown in FIG. 1, once the flexible sheet 12 is wrapped around the patient and secured in place by straps 24, the patient may be carried by emergency personnel by handles 30.

It is to be understood that the present invention is not limited to the embodiments described above, but encompasses any and all embodiments within the scope of the following claims.

I claim:

1. A spine immobilizing stretcher, comprising:
a flexible sheet having opposed upper and lower surfaces and being elongated in a longitudinal direction, the flexible sheet having a first and second laterally opposed side edges;
a single longitudinally extending sleeve formed on the upper surface of the flexible sheet, wherein the sleeve is formed solely within the middle of the flexible sheet and is coextensive the longitudinal extent thereof;
a plurality of straps secured to the first side edge of said flexible sheet, the plurality of straps being releasably securable to the second side edge of the flexible sheet; and
a stabilizing board removably received within the longitudinally extending sleeve, the stabilizing board being configured and sized to conform to the flexible sleeve, wherein the stabilizing board is longitudinally adjustable,
whereby the flexible sheet is configured to be slid under a patient suffering from spinal trauma such that the patient rests on the upper surface thereof and the patient's spine being positioned on and along the longitudinally extending sleeve, the stabilizing board then being inserted into the longitudinally extending sleeve to support and immobilize the patient's spine without moving the patient.

2. The spine immobilizing stretcher as recited in claim 1, further comprising a plurality of buckles secured to the second side edge of said flexible sheet for releasably engaging the plurality of straps.

3. The spine immobilizing stretcher as recited in claim 1, further comprising at least one first handle secured to the first side edge of said flexible sheet.

4. The spine immobilizing stretcher as recited in claim 3, further comprising at least one second handle secured to the second side edge of said flexible sheet.

5. The spine immobilizing stretcher as recited in claim 1, wherein said stabilizing board comprises at least two stabilizing members telescopically engaging one another.

6. The spine immobilizing stretcher as recited in claim 1, further comprising a cushion removably positioned on the upper surface of said flexible sheet for positioning between the legs of the patient.

* * * * *